United States Patent
McCord

(10) Patent No.: US 9,858,664 B2
(45) Date of Patent: Jan. 2, 2018

(54) SYSTEMS, PROCESSES, METHODS AND MACHINES FOR TRANSFORMING IMAGE DATA INTO SIZING AND VOLUME MEASUREMENTS FOR TISSUE

(71) Applicant: Roy McCord, Aliso Viejo, CA (US)

(72) Inventor: Roy McCord, Aliso Viejo, CA (US)

(73) Assignee: PRODO LABORATORIES, Aliso Viejo, CA (US)

( * ) Notice: Subject to any disclaimer, the term of this patent is extended or adjusted under 35 U.S.C. 154(b) by 0 days.

(21) Appl. No.: 15/055,463

(22) Filed: Feb. 26, 2016

(65) Prior Publication Data

US 2016/0180522 A1    Jun. 23, 2016

Related U.S. Application Data

(63) Continuation of application No. 14/052,003, filed on Oct. 11, 2013, now abandoned.

(60) Provisional application No. 61/720,153, filed on Oct. 30, 2012.

(51) Int. Cl.

| G06K 9/00 | (2006.01) |
| G06T 7/00 | (2017.01) |
| G01N 15/02 | (2006.01) |
| G02B 21/00 | (2006.01) |
| G06K 9/52 | (2006.01) |
| G06T 7/60 | (2017.01) |
| G01N 15/10 | (2006.01) |
| G01N 15/14 | (2006.01) |

(52) U.S. Cl.
CPC ........ *G06T 7/0012* (2013.01); *G01N 15/0211* (2013.01); *G01N 15/1463* (2013.01); *G02B 21/008* (2013.01); *G06K 9/00127* (2013.01); *G06K 9/52* (2013.01); *G06T 7/60* (2013.01); *G01N 2015/1006* (2013.01); *G01N 2015/1493* (2013.01)

(58) Field of Classification Search
None
See application file for complete search history.

(56) References Cited

U.S. PATENT DOCUMENTS

| 2009/0053182 A1* | 2/2009 | Ichim | A61K 35/545 |
| | | | 424/93.7 |
| 2009/0238438 A1* | 9/2009 | Wardlaw | G01N 33/49 |
| | | | 382/134 |
| 2012/0087919 A1* | 4/2012 | Schneider | C07H 21/04 |
| | | | 424/134.1 |
| 2013/0016885 A1* | 1/2013 | Tsujimoto | G06T 5/003 |
| | | | 382/128 |

* cited by examiner

*Primary Examiner* — Weiwen Yang
(74) *Attorney, Agent, or Firm* — Kirk Hahn

(57) ABSTRACT

Automated islet measurement systems (AIMS) in combination with tissue volume analysis (TVA) software effectively gauges volumetric and size-based data to generate heretofore unavailable information regarding, for example, populations of islet cells, stem cells and related desiderata.

3 Claims, 2 Drawing Sheets

| D (cm2/s)= | 1.00E-07 | integral | 1.00E-08 | integral | 1.00E-09 | integral | 1E-10 | integral | 1E-11 | integral |
|---|---|---|---|---|---|---|---|---|---|---|
| t (h)= | 24 | 2.08E-01 | 24 | 9.68E-02 | 24 | 3.08E-02 | 24 | 9.75E-03 | 24 | 2.91E-03 |
| x (mm) | c/co | Simpson terms | c/co | Simpson terms | c/co | Simpson terms | c/co | Simpson terms | c/co | Simpson terms |
| 0 | 1.000 | 1.000 | 1.000 | 1.000 | 1.000 | 1.000 | 1.000 | 1.000 | 1.000 | 1.000 |
| 0.02 | 0.988 | 3.951 | 0.962 | 3.847 | 0.879 | 3.516 | 0.630 | 2.522 | 0.128 | 0.513 |
| 0.04 | 0.976 | 1.951 | 0.923 | 1.847 | 0.761 | 1.522 | 0.336 | 0.672 | 0.002 | 0.005 |
| 0.06 | 0.964 | 3.854 | 0.885 | 3.541 | 0.648 | 2.592 | 0.149 | 0.596 | 0.000 | 0.000 |
| 0.08 | 0.951 | 1.903 | 0.847 | 1.695 | 0.543 | 1.086 | 0.054 | 0.109 | 0.000 | 0.000 |
| 0.1 | 0.939 | 3.757 | 0.810 | 3.240 | 0.447 | 1.787 | 0.016 | 0.065 | 0.000 | 0.000 |
| 0.12 | 0.927 | 1.855 | 0.773 | 1.546 | 0.361 | 0.723 | 0.004 | 0.008 | 0.000 | 0.000 |
| 0.14 | 0.915 | 3.661 | 0.736 | 2.945 | 0.287 | 1.147 | 0.001 | 0.003 | 0.000 | 0.000 |
| 0.16 | 0.903 | 1.806 | 0.700 | 1.401 | 0.224 | 0.447 | 0.000 | 0.000 | 0.000 | 0.000 |
| 0.18 | 0.891 | 3.564 | 0.665 | 2.660 | 0.171 | 0.684 | 0.000 | 0.000 | 0.000 | 0.000 |
| 0.2 | 0.879 | 1.758 | 0.630 | 1.261 | 0.128 | 0.256 | 0.000 | 0.000 | 0.000 | 0.000 |
| 0.22 | 0.867 | 3.468 | 0.597 | 2.387 | 0.094 | 0.377 | 0.000 | 0.000 | 0.000 | 0.000 |
| 0.24 | 0.855 | 1.710 | 0.564 | 1.127 | 0.068 | 0.136 | 0.000 | 0.000 | 0.000 | 0.000 |
| 0.26 | 0.843 | 3.373 | 0.532 | 2.127 | 0.048 | 0.192 | 0.000 | 0.000 | 0.000 | 0.000 |
| 0.28 | 0.831 | 1.663 | 0.501 | 1.001 | 0.033 | 0.066 | 0.000 | 0.000 | 0.000 | 0.000 |
| 0.3 | 0.819 | 3.278 | 0.470 | 1.882 | 0.022 | 0.090 | 0.000 | 0.000 | 0.000 | 0.000 |
| 0.32 | 0.808 | 1.615 | 0.441 | 0.883 | 0.015 | 0.030 | 0.000 | 0.000 | 0.000 | 0.000 |
| 0.34 | 0.796 | 3.184 | 0.413 | 1.654 | 0.010 | 0.039 | 0.000 | 0.000 | 0.000 | 0.000 |
| 0.36 | 0.784 | 1.568 | 0.386 | 0.773 | 0.006 | 0.012 | 0.000 | 0.000 | 0.000 | 0.000 |
| 0.38 | 0.773 | 3.090 | 0.361 | 1.443 | 0.004 | 0.015 | 0.000 | 0.000 | 0.000 | 0.000 |
| 0.4 | 0.761 | 1.522 | 0.336 | 0.672 | 0.002 | 0.005 | 0.000 | 0.000 | 0.000 | 0.000 |
| 0.42 | 0.749 | 2.997 | 0.312 | 1.249 | 0.001 | 0.006 | 0.000 | 0.000 | 0.000 | 0.000 |
| 0.44 | 0.738 | 1.476 | 0.290 | 0.580 | 0.001 | 0.002 | 0.000 | 0.000 | 0.000 | 0.000 |
| 0.46 | 0.726 | 2.906 | 0.268 | 1.074 | 0.000 | 0.002 | 0.000 | 0.000 | 0.000 | 0.000 |
| 0.48 | 0.715 | 1.430 | 0.248 | 0.496 | 0.000 | 0.001 | 0.000 | 0.000 | 0.000 | 0.000 |

Figure 2

SYSTEMS, PROCESSES, METHODS AND MACHINES FOR TRANSFORMING IMAGE DATA INTO SIZING AND VOLUME MEASUREMENTS FOR TISSUE

CROSS-REFERENCE TO RELATED APPLICATIONS

This application claims the full Paris Convention benefit and is a Continuation of U.S. Non-Provisional Application Ser. No. 14/052,003 filed on Oct. 11, 2013, which claims priority of U.S. Provisional Application Ser. No. 61/720,153, filed Oct. 30, 2012, the contents of which are incorporated by this reference as if fully set forth herein. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

BACKGROUND OF THE DISCLOSURE

Various tissue elements and other biological matter require precise data to support characterization, culturing and rendering the same effect for important usages and purposes. Optical imagery likewise provides a powerful tool.

Those skilled in the art readily understand that a first step in managing sensitive tissue can be found by capturing image data and arraying the same for various purposes.

According to the instant disclosures, scanning imagery technology, improved algorithms and alternate optical techniques may be used to inventively gauge, measure and validate aspects of tissue measurement, by volume.

OBJECTS AND SUMMARY OF THE DISCLOSURE

Briefly stated, automated islet measurement systems (AIMS) in combination with tissue volume analysis (TVA) software effectively gauges volumetric and size-based data to generate heretofore unavailable information regarding, for example, populations of islet cells, stem cells and related desiderata.

According to embodiments, there is disclosed an automatic tissue scanning camera (ATSC) system and methods to measure sizes and volumes of, for example, populations of islet cells within a culture flask.

According to embodiments, there is disclosed a system comprising tissue volume analysis (TVA) software, using thresholding to identify individual cells, for example islet cells, and to evaluate cross-sectional linear size of cells, for example islet cells, via an algorithmic simulacrum of manual counting under microscopy.

According to embodiments, there is disclosed a system, wherein said TVA software measures the optical transmission of each pixel within each cell, for example islet cell, using this to calculate thickness of tissue at that pixel based upon optical extinction; and, based on constant pixel area, calculates volume represented by respective pixels; whereby voxels, volume elements, are then summed to generate resultory total cell, for example islet cell, volume.

According to embodiments, there is disclosed a system wherein an automated image measurement algorithm, as defined in Appendix A, is employed.

According to embodiments, there is disclosed a process for generating sizing and volume measurement data by transforming optical imagery, comprising, in combination: providing an AIMS/imaging apparatus/scanner; having TVA algorithms and related software disposed therein; imaging at least a cell; generating predetermined fields for sizing and volume; conforming, registering and (or otherwise validating) the resultory data; and, using the same to create information which can be further compared to laser transaction microscopy and diffusing measurement data to confirm resulting data sets.

According to embodiments, there is disclosed a machine for transforming optical data into cellular sizing and volume measurement information, whereby scanned images are assembled further comprising at least one of islets and spheres of stem cells; and, in an independent unit validating the same, whereby confocal microscopy, likewise capable of diffusing measure, enables optical slicing of images of said islets and spheres of stem cells horizontally, using scattered light to document the subject area, which multiplied by thickness generates an independent validation of the volume generated by said machine.

BRIEF DESCRIPTION OF THE FIGURES

FIG. 2 is a table distribution into depth X of permeant in a thin membrane.

DETAILED DESCRIPTION OF THE DISCLOSURE

Figure 1:
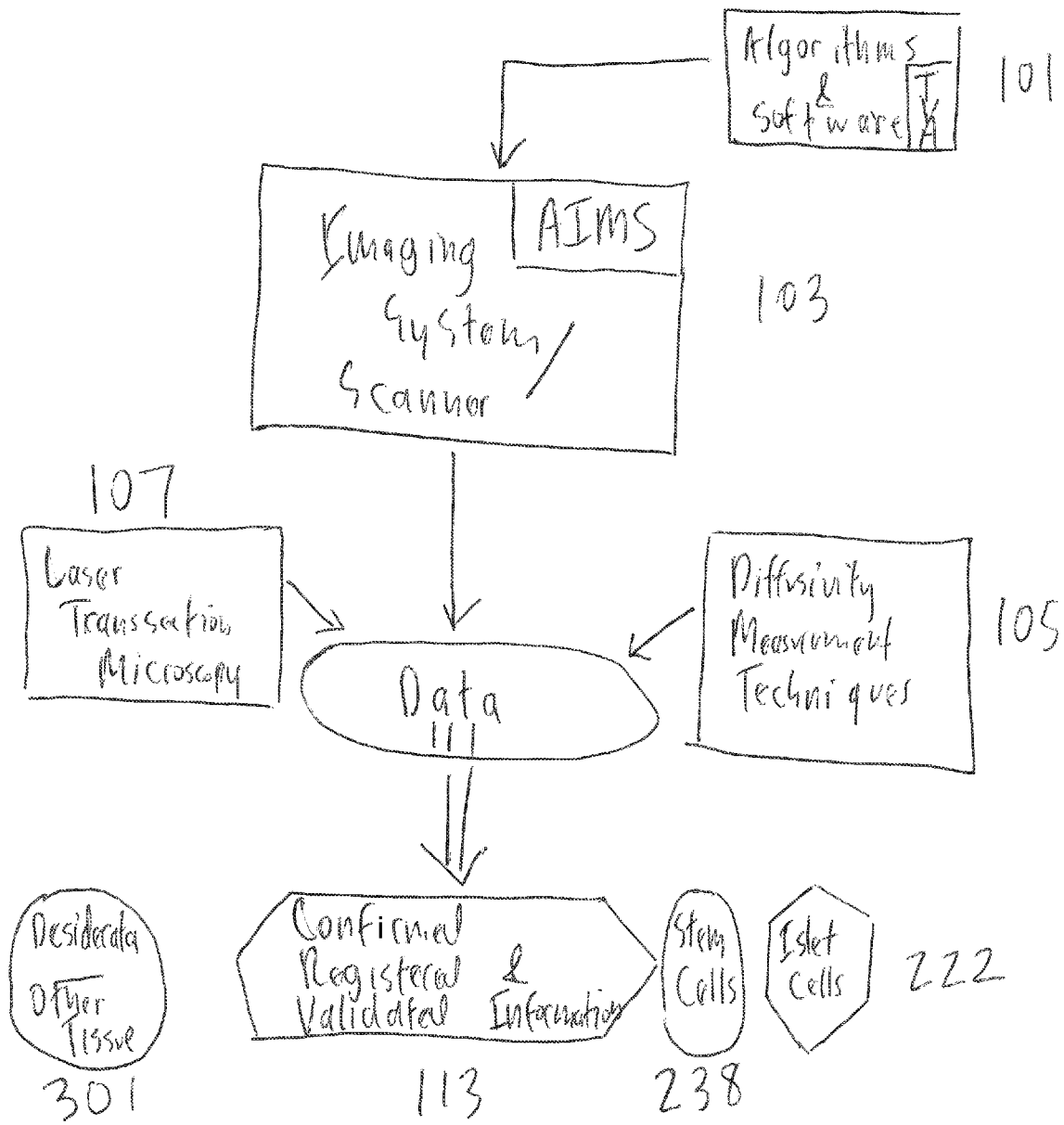
FIG. 1 is a schematic block/flow diagram showing operation of systems, methods, processes and products by the processes, according to the instant disclosures.

Expressly incorporated herein by reference are U.S. Letters Pat. Nos. 8,211,697; 8,213,081; 8,228,499; 8,293,223; 8,236,281; and 8,288,339.

The present inventor has discovered how to use new combinations of optical tools to characterize heretofore un-cognizable configurations of cells, constituents thereof and related desiderata having extensive implications.

Referring now to FIG. 1 and FIG. 2, algorithms embedded within software are accessed (including by remote, wireless and other means known or developed) to drive AIMS/imaging system/scanner 103, which generates data 111 regarding sizing and volume of subject cells, for example, islet cells (as described in Appendices A and B, for example).

Said data 111 is useful for characterizing the physical nature of subject cells, in this case, islet cells, whose spatial orientation and related behavior can now be understood as driven by data 111 and confirmed and registered with validated information—such as the more ellipsoid nature of the islet cells. Likewise, tissue transection microscopy 107 and diffusing measurement technologies, can be used to confirm these findings.

The Volume Measurement Algorithm for Individual Islets: This is a brief summary of the Automated Image Measurement Algorithm for measurement of tissue volumes. This system is based on the following considerations.

The volume of a right parallelepiped may be expressed as:
$V = A \times h$

The volume of an arbitrary object can be approximated by summing the discrete element volumes of the small parallelepipeds with uniform cross-section area, A, and height, h, that compose it: $V=\Sigma(A \times h)$ The digital image of an object is a construction of rectangles whose individual areas in the image are from individual pixels each representing a specific area in object space (dependent on, for instance, "magnification").

For absorption microscopy of biological tissues (i.e. non-phase contrast microscopy) without the use of stains, the 20 image corresponds to the optical "shadow" cross-section. The individual pixel measurements are a function of the thickness and the optical absorption of the tissue along the optical axis (this approximation is valid for thin sections) as described by the Lambert-Beers Law: $Ip=I0 \exp(-a \times tp)$ where Ip is the intensity measured by a pixel imaging tissue, $I0$ is the intensity of illumination and tp is the tissue thickness. Local optical transmission can be defined as $T_P = I_p/I_0$ so that $T_P = (-\ln T_P)/\alpha$; where $\alpha$=absorption coefficient.

Since the volume of an object can be represented by: $V_0 = \Sigma(A_p \times t_p)$; where the area and thickness are for individual pixels representing the object; space, the volume may be calculated from the digital optical image of the object: $V_0 = \Sigma(A_p \times (-\ln T_p)/\alpha)$. $V_0 = \Sigma(A_p \times \{-\ln(I_p/I_0)\}/\alpha)$.

Uncertainty Analysis—Individual Volumes: The uncertainty of the area of an individual pixel in object space is dependent on the uncertainty of measurement of the microscope field size. This uncertainty is less than 2% (20 microns in a 3 mm field size). $\Sigma(A_p \times t_p)$ Thresholding: Objects are identified by binary thresholding so the summation uncertainty is dependent on thresholding: only pixels that are below a threshold intensity are identified as part of an object (particle detection) therefore exclusion of light areas in objects undercounts pixels in the summation. A binary closing function fills light areas identified as "holes" in objects so this defect will only affect thin portions surrounding the outer fringe of identified objects. The effect of thresholding has been evaluated functionally by measuring objects with thresholds set significantly above and below optimal (>6 units in approximately 130). The variation of measured volume between threshold extremes and optimal is less than 10%.

Calibration to micro-spheres: We have assessed particle detection and measurement reliability by comparing particle measurements with the image analysis system to NIST-traceable specifications for Coulter Counter calibrating spheres. The measurement of particle size (area) using image analysis compares very closely with the specifications for calibrating spheres.

$T_P = I_p/I_0$—measurement of light intensity: Light intensity measurement with CCDs: CCD pixel outputs are individually linear over many decades of illumination intensity. We correct for CCD pixel-to-pixel sensitivity and local variations of illumination and viewing response by flat-field image processing on all images prior to extraction of digital information. The flat field image, reflecting the effects of illumination, optics and the CCD, has a typical standard deviation of approximately 3% (6 parts in 200). After flat field correction this non-uniformity is reduced to virtually zero.

Test of linearity: Linearity has been confirmed (by use of overlapping calibrated density filters) to be on average within +/−2% over the range of intensity measurements of interest.

Algorithm for measuring transmission: The measurement of background intensity, $I_0$, is based on averaging the measured intensity of light in a ring around each identified object. The ring is created by a series of 3-pixel wide object dilations followed by image subtraction. Errors in this measurement can arise if any field darkening, in particular by an adjacent particle, lies close enough to be within the ring. Our object image density is low (<1%) so this has not been observed to be a problem. This technique for measuring background minimizes the effect of light intensity variations locally per image and over the time of image acquisition.

Effect of focus: The accurate measurement of intensity by microscope is affected by focussing. Objects above or below the focal plane lose "contrast", that is, approach the brightness of the background. We have measured the effect of placing the focus above and below object tissue masses, that is, above and below the nominally perceived best-focus position. The worst-case out-of-focus condition changes measured tissue mass by less than 10%. Since tissue typically settles rapidly to the bottom of the flask, this effect has the beneficial effect of helping to discriminate against out-of-focus non-tissue image artifacts such as floating fragments or outer flask wall defects; the threshold eliminates lightened artifacts.

Measurement of the absorption coefficient: The optical darkening that makes an object tissue visible in non-phase contrast microscopy is due to absorption of chromophores native to the object. For thin sections, where scattering is negligible, the average absorption is describable by the absorption coefficient, a. We have measured an average a for islet tissues and for NIT cells by measuring transmission of tissue at 650 nm captured in known spaces between microscope slides. The coefficient measured varies between 0.0033 um−1 and 0.0051 um−1 (see attached figure "measurement of absorption coefficient"). These numbers compare favorably to values in the literature for other tissues at this wavelength.

Specific value: For calculation of volume we have adopted the average value of 0.0033 um−1. For detection of relative changes in tissue volume over time, this consistent use of a single value is required.

Use of average absorption coefficient: The absorption coefficient varies for specific morphological features of a tissue. To minimize this effect we have chosen monochromatic, long-wavelength, visible light for illumination because generally the absorption coefficient for biological tissues decreases and converges for longer red wavelengths.

To evaluate the use of the average absorption coefficient algorithm, we squeezed NIT cells between microscope slides separated by rigid spheres of known size. The consequently flat, parallel-sided tissue disks were measured for volume by optical imaging. This was compared to calculation of volume as area times thickness. The regression (see figure "test algorithm") was essentially a straight line, which confirms the use of an average coefficient for thickness calculation.

Test of volume measurement: The ability to accurately measure the volume of a single object was tested by imaging a plate-like porcine islet manipulated to edge-on and face-on positions. The difference in thicknesses presented by the two different views is a test of the validity of our optical transmission thickness measurement algorithm. Linear dimensions measured using the microscope image versus transmission were within 4% of each other and volumes measured were within 6% of each other (see attached figure "camps by view" and corresponding images).

Overall uncertainty of individual islet volume measurement: Based on the above the uncertainty of measurement of relative individual islet volumes is estimated to be less than 15%. The estimate of absolute volume measurement is dependent on further characterization of the absorption coefficient.

A flask containing a population of particles may be characterized by optical sampling. Since all the islets quickly settle to the bottom of our flasks, we can obtain an accurate sample of the population by imaging as much of the flask area as possible. The accuracy of this sampling is governed by sampling statistics where our population is non-homogeneous in particle size. The volume characteristics of the population can be calculated: $V_K = V_{Ks} \times S_K$.

Where $V_K$ is the volume (or number) of islets in a histogram size bin K and $V_{Ks}$ is the volume (or number) measured by optical sampling and $S_K$ is the sample multiplier for a given bin. The sample multiplier is: $S_K = 1/P = A_F/(A_{im} \times m)$.

Where P is the fraction of the bottom of the flask which is sample by images, $A_F$ is the area of the flask bottom and $A_{im}$ is the object-area of one image and m is the number of non-overlapping images taken. For our work P has been between 0.05 and 0.40 (currently about 10% sampling). The total volume in a flask is calculated: $V_T = \Sigma V_K$.

The uncertainty of sample analysis is based on sampling statistics. The uncertainty of a bin sample is inversely proportional to the square root of n, where n is the number of particles in a given bin. We have tested the sampling variations by measuring several times in succession a flask containing microspheres. The average fractional range (maximum to minimum divided by the average) for eight series was 6.3%.

We have compared the measurement results of image analysis particle counting to results with the Coulter Counter using identical samples of calibrated microspheres. The image analysis count was approximately 15% low for 68 micron diameter spheres and was identical for 200 micron spheres (see attached figure "compare Coulter to IA beads"). We have tested the sampling variations for tissue by measuring several times in succession a flask containing human islets. Preliminary results show similar consistency, although, as expected, the sampling uncertainty increases for larger size particles because the population contains ever fewer large volume particles.

Artisans readily understand the nature and extent of the instant system to be useful for stem cells and related desiderata.

Returning to islet cells, it has long been assumed that a generally spherical configuration was in play, impacting numerous empirical aspects of their storage, usage, and other key issues. Using the teachings of the present disclosure, the ellipsoid (or, American "football-like") shape of islet cells was confirmed, enabling ongoing research heretofore uncontemplated as currently understood. Such teachings comprise progress in science and the useful arts, and likewise present subject matters for U.S. Letters Patents.

While the method and apparatus have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Merriam-Webster's Unabridged Dictionary, the latest edition of which is hereby incorporated by reference.

Finally, all references listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant.

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. An automatic tissue scanning camera (ATSC) system, which comprises, in combination:
    a non-phase contrast microscope;
    a monochrome charge-coupled device (CCD) camera;
    a horizontally-mounted culture flask;
    a trans-illumination means, which exceeds the deep field image size by a factor of at least two; and
    an automated islet measurement system (AIMS), comprising tissue volume analysis (TVA) software, the AIMS configured to:
        identify a cell in the culture flask, wherein opposing surfaces of the culture flask do not deform the cell;
        image the cell with the camera, wherein the cell has a natural, undeformed by a mechanical force, shape, the image comprising pixels;
        evaluate a cross-section size of the cell;
        measure an optical transmission at each pixel within the cell;
        calculate a volume of tissue at each pixel; and
        calculate a total volume for the cell.

2. The automatic tissue scanning camera (ATSC) system of claim 1, wherein the cell is an islet.

3. The automatic tissue scanning camera (ATSC) system of claim 1, wherein the cell is a stem cell.

* * * * *